(12) United States Patent
Eliav et al.

(10) Patent No.: US 6,848,141 B2
(45) Date of Patent: Feb. 1, 2005

(54) BRUSH SECTION FOR AN ELECTRIC TOOTHBRUSH

(75) Inventors: Eyal Eliav, New York, NY (US); Kyoungeun Ahn, New York, NY (US); John J. Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 194 days.

(21) Appl. No.: 09/878,036

(22) Filed: Jun. 8, 2001

(65) Prior Publication Data

US 2002/0184719 A1 Dec. 12, 2002

(51) Int. Cl.[7] .............................................. A61C 17/34
(52) U.S. Cl. .................. 15/22.1; 15/167.1; 15/DIG. 5; D4/101

(58) Field of Search .................................. 15/22.1, 22.2, 15/22.4, 28, 29, 167.1, DIG. 5; D4/101, 104, 112, 109, 111

(56) References Cited

U.S. PATENT DOCUMENTS 6,308,358 B2 * 10/2001 Gruber et al. ............... 15/22.1
6,463,615 B1 * 10/2002 Gruber et al. ............... 15/22.1
6,510,575 B2 *  1/2003 Calabrese ................... 15/22.1

\* cited by examiner

*Primary Examiner*—Mark Spisich
(74) *Attorney, Agent, or Firm*—Harris A. Wolin; Clifford E. Wilkins

(57) ABSTRACT

An electric toothbrush brush section and method of use thereof is disclosed, the brush section having a generally disk shaped bristle carrier from which extend one or more bristle bearing fingers of varying length and width, which fingers provide increased contact area between bristles and oral gingival tissue for enhanced massaging thereof.

13 Claims, 8 Drawing Sheets

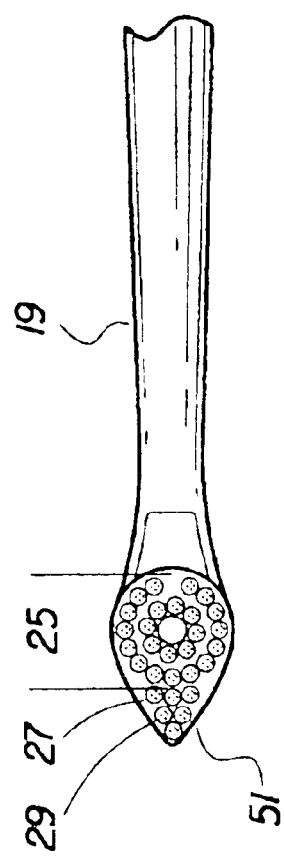
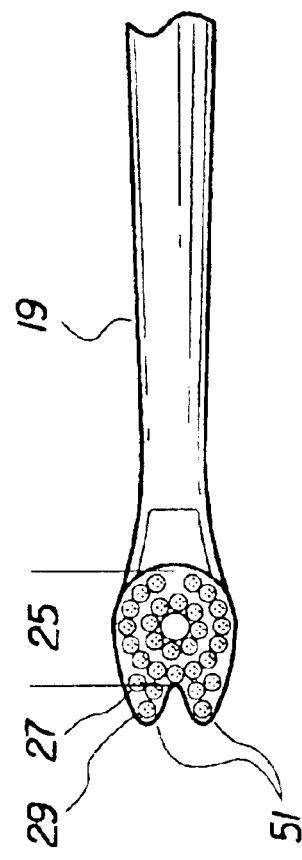
FIG. 3
FIG. 4

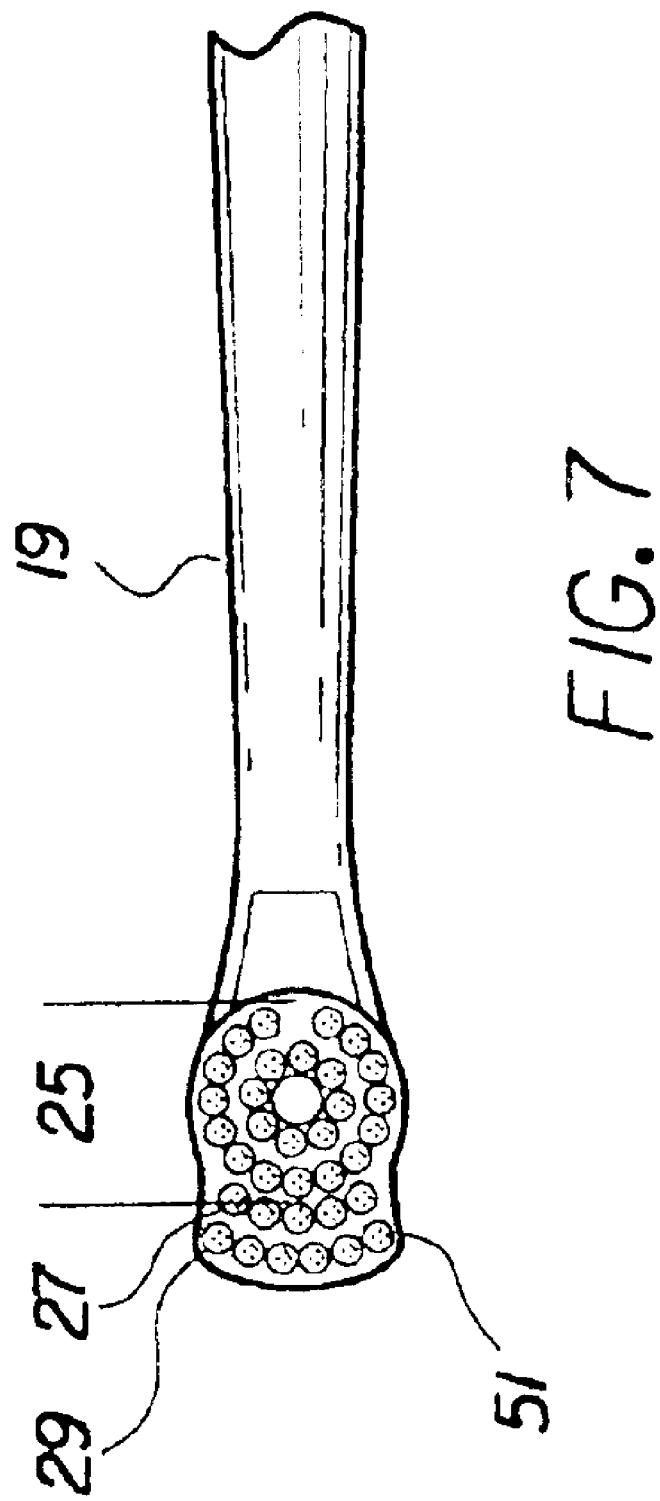

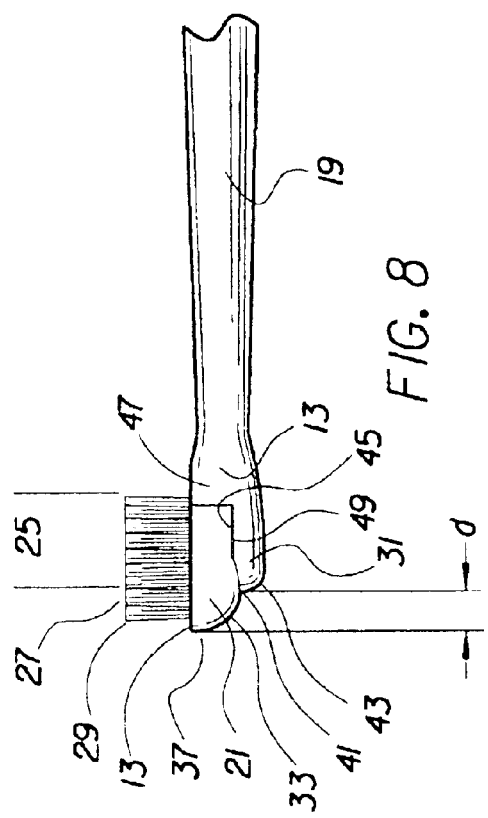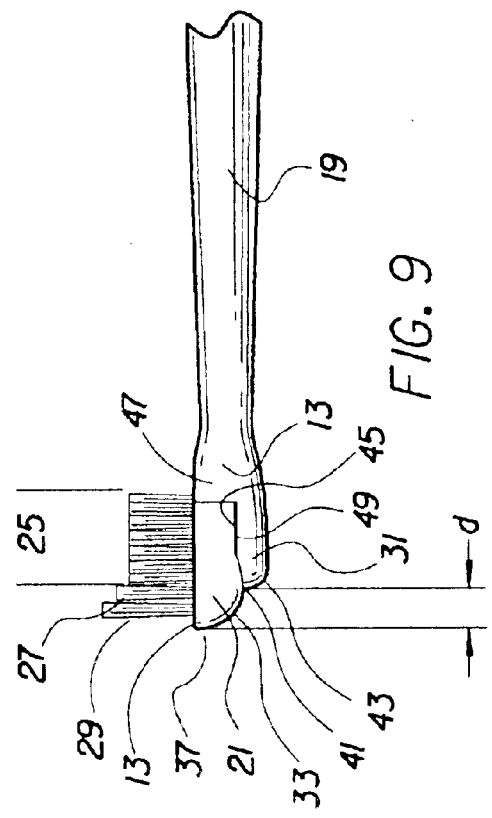

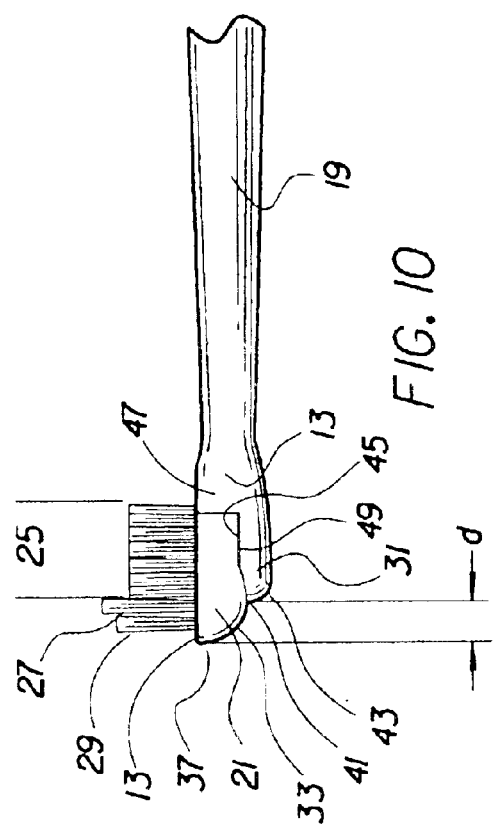
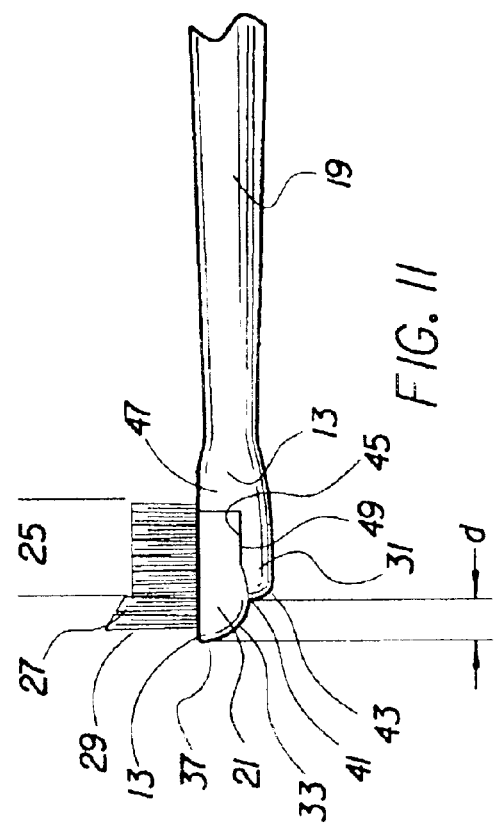

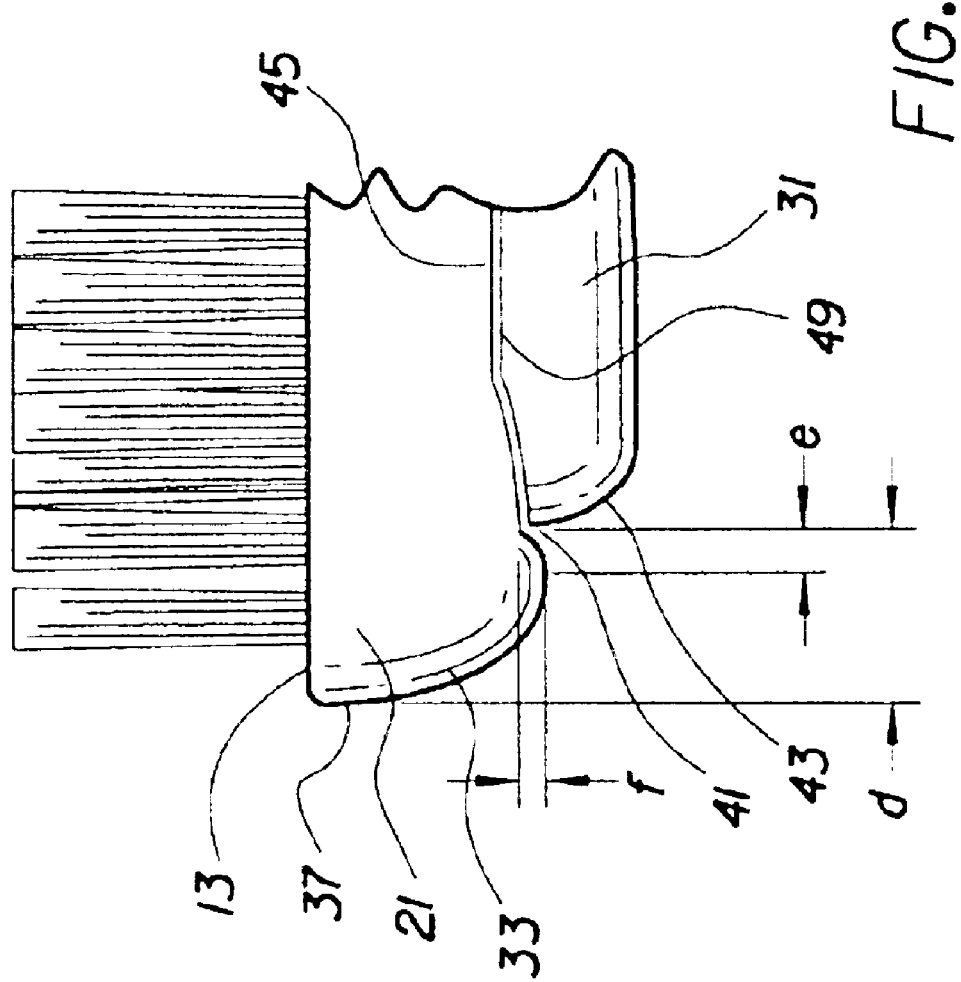

BRUSH SECTION FOR AN ELECTRIC TOOTHBRUSH

BACKGROUND OF THE INVENTION

1. Field of the Invention

The present invention relates to a brush section for an electrically powered toothbrush and a method of use thereof, and more particularly to such a brush section having a partially disk shaped bristle carrier that has one or more bristle bearing protuberances or fingers extending therefrom, whereby in use the bristles on the extended fingers will provide increased contact with the oral gingival tissue for enhanced massaging thereof.

2. The Prior Art

It is well understood in the art that toothbrushes provide three major benefits, removal of plaque and food debris, to help in avoiding tooth decay and disease; removal of the stained pellicle on the surface of each tooth, for whitening; and massage, for stimulation and health of the gingival tissue. To achieve these benefits, manual toothbrushes which historically were produced with a flat trimmed bristle pattern are today commercially available with a myriad of alternative bristle patterns, such as, for example, disclosed in U.S. Pat. No. 5,341,537, U.S. Des. 387,562, and WO 99/23910.

The bristles of electric toothbrush are conventionally arranged in compact conical or cylindrical patterns on generally circular, disk shaped bristle carriers, as disclosed in U.S. Pat. Nos. 2,215,031 and 5,467,495, respectively. U.S. Pat. No. 5,465,444 discloses an alternative, still relatively compact, generally oval bristle support and bristle pattern. Other alternative bristle patterns and carrier shapes are disclosed in U.S. Pat. No. 5,862,559, still relatively compact, which include a pyramidal shape bristle pattern on a square carrier. Such compact bristle patterns provide efficient transfer of the rotation or oscillation motion of the electric toothbrush to the surface of each tooth to remove the build-up of plaque, debris, and stained pellicle therefrom; while minimizing the load on the brush motor to maximizing the battery life in battery powered electric toothbrushes. Such compact bristle patterns do not however, adequately provide for the third benefit desired of a toothbrush, that is the massage of the gingival tissue for the health thereof.

U.S. Pat. No. 5,836,030 and U.S. Des. 397,252 disclose an electric toothbrush having a cylindrical bristle pattern extending from a first circular, or disk shaped bristle carrier with a first pivotal axis; and a second bristle carrier adjacent to the first bristle carrier, with rows of bristles tufts extending therefrom; which second bristle carrier reciprocates about a second pivotal axis. The cylindrical bristle pattern provides the conventional cleaning of the each tooth surface; while the rows of bristles tufts extending from the second bristle carrier provide cleaning within the interdental spaces. To provide such separate bristle carriers, with such separate motion requires a relatively complex drive mechanism.

There is a need in the art for an alternative electric toothbrush, with a relatively simple design which is relatively compact, to provide the benefits of removal of plaque, debris and stained pellicle from the tooth surfaces, while also providing enhanced massaging of the gingival tissue.

SUMMARY OF THE INVENTION

The present invention provides a brush section for an electric toothbrush and a method for use thereof, which brush section has at a first end a connector adapted to be joined to an electric toothbrush handle section and at the other end has a head, which head terminates in a toe; the head contains a bristle carrier which has a first portion closest to said first end which is generally disk shaped with a circular cross-section; said circular cross-section is broken by one or more protuberances or fingers extending therefrom in a direction generally distal to said first end; the bristle carrier having a face extending across said first portion and across said one or more fingers, from which face extends a plurality of bristle tufts; wherein said face is not circular or oval in shape; the handle section being arranged to contain a drive means which is drivingly engaged to said carrier; whereby in use as said carrier is oscillatingly or reciprocatingly driven, the bristles on the one or more fingers will provide increased contact with the oral gingival tissue for enhanced massaging thereof.

In a further embodiment of the present invention, the bristle carrier ends in one narrowed finger, such that the bristle carrier has a generally egg-shape face, from which face extend a plurality of bristles arranged in generally concentric rings of bristle tufts about the generally circular portion of the egg-shape, and wherein a plurality of bristle tufts are arranged in rows, which may be arcuate, on the finger portion thereof. The bristle tufts comprising the rows of bristles on the finger portion may be longer than the bristles within the concentric rings of bristle tufts, to extend into the interproximal spaces between the teeth for enhanced cleaning therein.

BRIEF DESCRIPTION OF THE DRAWINGS

For a fuller understanding of the nature of the invention, reference the following detailed description, taken in connection with the accompanying drawings in which:

FIG. 3 is a front elevation showing a second embodiment of the brush section of the present invention, which is similar to the embodiment of FIGS. 1 and 2, in that the brush section has a generally egg-shaped face.

FIG. 4 is a front elevation showing a third embodiment of the brush section of the present invention wherein two bristle bearing fingers extend from the generally disk shaped body thereof.

FIG. 7 is a front elevation showing a sixth embodiment of the present invention containing another one bristle bearing alternative, which differs from the other one finger embodiments in the extended width of the finger shown.

FIG. 8 is a side elevation showing a flat bristle trim, applicable to any one finger embodiment of the present invention, such as shown in FIG. 1, 2, 3, 6 or 7.

FIG. 9 is a side elevation of the embodiments in FIG. 8, wherein the two rows of bristle tufts located on the finger portion of the brush face have a stepped trim.

FIG. 10 is a side elevation of an alternative embodiment of the present invention, similar to the embodiment of FIG. 9, except reversing the height order of the stepped trim of the bristle tufts within the rows of bristles located on the finger portion of the brush face.

FIG. 11 is a side elevation showing an alternative stepped trim embodiment of the present invention, similar to that within FIG. 9; except, the ends of the stepped bristle rows are chamfered or beveled toward the toe of the toothbrush.

FIG. 12 is an enlargement of the toe portion of the side elevation of a typical embodiment of the present invention, such as that shown in FIG. 8, to highlight the physical configuration of the toe portions of the bristle carrier and the bristle carrier support; an arrangement provided to avoid pinching of the user within the separation therebetween.

DETAILED DESCRIPTION

Figure 1:
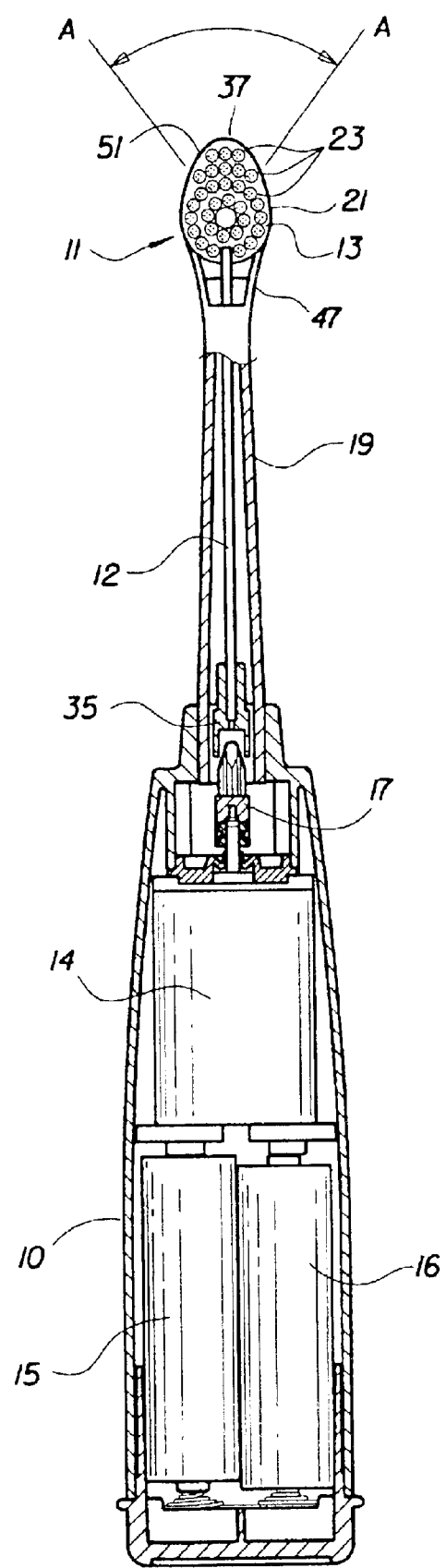
FIG. 1 is front elevation showing a first embodiment with a brush section of the present invention that has a generally egg-shaped face; the brush section being mounted on a cut-away view of a conventional electric toothbrush handle.

Reference is made to FIG. 1, showing a first embodiment of an electric toothbrush 11 having a brush section 19 of the present invention, which brush section 19 has at a first end a connector 35 adapted to be joined to a handle section 10, and at the other end is a head 47 which terminates in a toe 37; which connector 35 and which head 47 may be generally aligned along the longitudinal axis of the toothbrush 11; which head 47 contains a bristle carrier 21 having a first portion 25 closest to said first end, which first portion 25 is generally disk shaped with a circular cross-section that is broken by a protuberance or finger 51 extending therefrom in a direction generally distal to said first end; a face 13 extends from and across said first portion 25, to and across said finger 51; from which face 13 extends a plurality of bristle tufts; said bristle carrier 21 having a generally egg-shaped bristle bearing face 13. The handle section 10 is adapted to contain batteries 15,16, to power a motor 14; which motor 14 is a coupled by a coupling mechanism 17 to a drive shaft 12 located within the brush section 19, to drive said bristle carrier 21 in a oscillating or reciprocating manner, shown as arc A—A about the longitudinal axis of the toothbrush. The oscillation or reciprocation of the bristle carrier may be at least 120 degrees in arc A—A, preferably at least about 90 degrees in arc A—A and more preferably at least about 30 degrees in arc A—A and most preferably at least about 15 degrees in arc A—A. Further, the brush section 19 may be demountable from the handle section 10, as shown in FIG. 1, or it may alternatively be permanently attached thereto, i.e. wherein the brush section 19 and the handle section 10 are manufactured as one integral unit, as for example disclosed in U.S. Pat. No. 6,178, 579.

Figure 2:
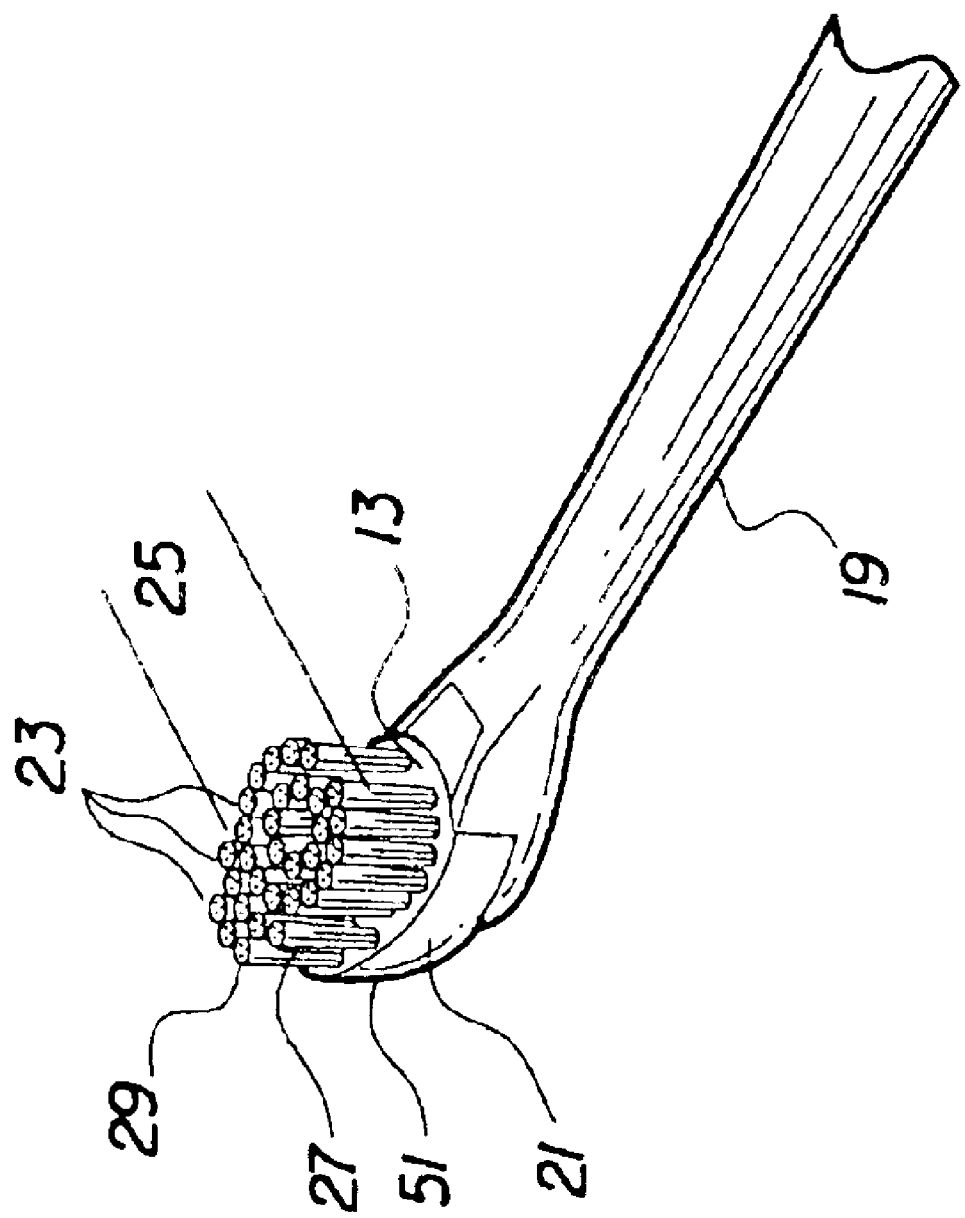
FIG. 2 is a perspective view of the brush section with the generally egg-shaped face of FIG. 1.

FIG. 2 is a perspective view of the bristle bearing end of the brush section 19 of the toothbrush of FIG. 1, wherein bristle carrier 21 with a generally egg-shaped face 13 is shown with a plurality of bristle tufts 23 extending therefrom. As shown, the bristle tufts 23 substantively cover the entirety of the footprint of the egg-shaped bristle carrier 21, such that any cross-section of the bristles tufts corresponds in form to the generally egg-shaped face 13 of the underlying bristle carrier 21. The bristles may be arranged in two groupings of discrete tufts, as shown in FIG. 2; the first grouping being located about the circular cross-section of the first portion 25 of the generally disk shaped portion of the generally egg-shaped bristle carrier 21, in concentric rows; the second grouping located within the finger 51 portion of the bristle carrier 21 may be composed of one, two or more linear or arcuate rows of bristles 27, 29.

Figure 5:
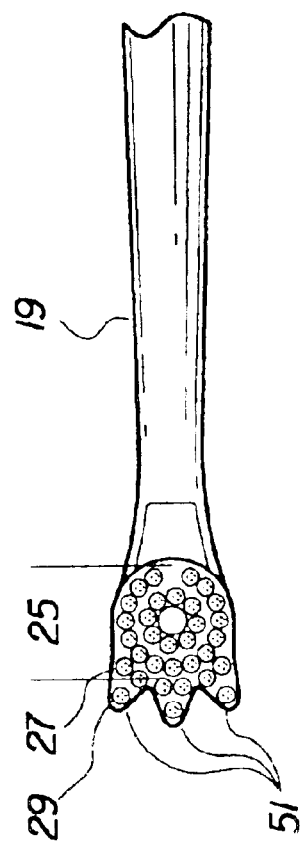
FIG. 5 is a front elevation showing a fourth embodiment of the brush section of the present invention, wherein three bristle bearing fingers extend from the generally disk shaped body thereof.
Figure 6:
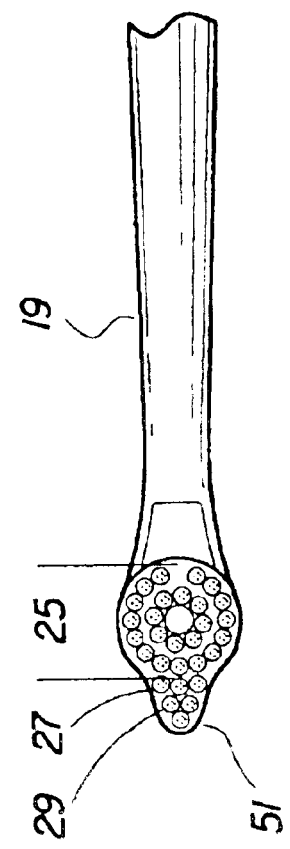
FIG. 6 is a front elevation showing a fifth embodiment of the brush section of the present invention wherein one bristle bearing finger extends from the generally disk shaped body thereof, which differs from the embodiments of FIGS. 1 and 3 in that the brush section does not have a generally egg-shaped face.

The front elevations of FIGS. 3, 4 and 5, contain alternative embodiments of the present invention which terminate in one, two or three fingers 51, respectively, extending from generally disk-shaped bristle carriers 21. The length and width of the face portion of each finger 51 can be varied; as for example in FIGS. 3 and 6, showing narrower one fingered embodiments and in FIG. 7 showing a broader one finger embodiment. The length and width of any finger 51 is such that the face 13 of the bristle carrier 21 will not be circular or oval in shape. The choice to utilize a greater number of fingers 51 and/or longer or wider fingers 51 to provide additional bristle area for enhanced massaging of the gingival tissue, must be balanced against the load on the batteries 15, 16 and the resultant effect on battery life.

As shown in the embodiments of FIGS. 1 through 7 of the present invention, the bristle pattern of the first grouping of bristle tufts, located within the partially disk shaped first portion 25 of the bristle carrier 21 closest to the connector 35, is preferably arranged in a series of concentric rows. The innermost row or rows within this concentric grouping of bristle tufts, may be shorter than the rows closer to the outer perimeter of the grouping, to provide a depression in surface of the concentric grouping to better retain toothpaste thereon.

As illustrated in the embodiments of FIGS. 8 through 10 of the present invention, the rows of bristle tufts 27, 29 nearest the toe end 37 of the brush section 19, can be of uniform height or can varying height, i.e. a stepped trim. Preferably, these rows of bristle tufts 27, 29, are taller than the other rows of bristles extending from the bristle carrier 21. Further, as shown in FIG. 11, the ends of these rows of bristles tufts 27, 29 can be chamfered or beveled at an angle to form a point either toward the toe end of the brush section 19 (as shown in FIG. 11) or away therefrom (not shown). The stepped end trim shown in FIGS. 9 and 10 or of the chamfered end trim, as shown for example in FIG. 11, allows the elongated and/or elongated and angled bristles to will more easily penetrate into the interproximal spaces between the teeth for cleaning therein.

As shown in the embodiments of FIGS. 8 through 12 of the present invention, the bristle carrier has a bottom surface 45, which is opposite to the face 13 from which the bristles tufts 23 extend. Spaced away from and adjacent to the bottom surface 45 is a bristle carrier support 31, which carrier support 31 has a first end integral with the head 47 and a second free, toe end 43. The bristle carrier 21 may be rotationally supported by means of a conventional central, rotational supporting shaft, axis, or axial pin (means not shown herein) which extends from the upper surface 49 of the bristle support 31 to the bottom surface 45, as is disclosed and described in U.S. Pat. Nos. 6,092,252, 5,784, 743, 5,732,432. As shown in FIGS. 8 through 12, the toe 37 of the bristle carrier 21 extends past the free toe end 43 of the carrier support 31 by a distance d, which may be up to 5 mm or more.

As shown in FIG. 12, an enlargement of the end portion of the brush head 47 of the present invention, between the bottom surface 45 of the bristle carrier 21 and the free, toe end 43 of the bristle carrier support 31 is an interface or separation 41, within which the users lip or cheek may be pinched. To prevent such pinching, the front edge 33 of the bottom surface of the bristle carrier 21 is curved outward, i.e. the front edge 33 is convex with respect to said connector 35 and arcs transversely further from the longitudinal axis of said toothbrush 11 than any point on the upper surface (49) of said bristle support carrier 31. The convex arc of said front edge 33 may extend past the separation 41 by a distance f, at least about 0.5 mm, and forward of the separation by a distance e, at least about 0.75 mm. The radius of curvature of the front edge of the bottom surface 33 should be at least about 1 mm and preferably at least about 1.5 mm. Further, the free toe portion 43 of the bristle carrier 31 is itself curved convexly with respect to said connector 35, with a radius of curvature of at least about 0.5 mm and preferably at least about 1 mm.

The means by which electric toothbrushes provide swiveling, gyrating, oscillating or reciprocating motion to drive the bristle carrier, such as the bristle carrier 21 of the present invention are well known in the art and include such means as those disclosed in the patents cited above and in U.S. Pat. Nos. 6,178,579, 5,625,916, 5,504,961 and 5,054,149. The power source used for such toothbrushes and for the toothbrush of the present invention can include single use or rechargeable batteries, or a line cord to connect to a standard wall power outlet.

What is claimed is:

1. A brush section for an electric powered toothbrush comprising, a first end having a connector adapted to be joined to a handle section; and a second end containing a head, which head terminates in a toe;

said head containing a bristle carrier with a first portion closest to said first end, which first portion is generally disk shaped with a generally circular cross-section;

said first portion has one or more fingers extending therefrom, in a direction generally distal from said first end;

said bristle carrier has a face extending across said first portion and across said one or more fingers, from which face extends a plurality of bristle tufts;

wherein said face has a shape other than circular or oval;

said handle section contains a driving means which is drivingly engaged to said bristle carrier;

whereby in use, the bristles extending from the one or more fingers provides increased contact with the gingival tissues and enhanced massaging thereof, wherein the bristle carrier has a bottom surface opposite to said face, which bottom surface has a front edge, said bottom surface is attached to the center of said bristle carrier by a rotational supporting means to a bristle carrier support; said bottom surface of the bristle carrier is attached to a bristle carrier support by a rotational supporting means;

which bristle carrier support has a first end integral with the head and a second free, toe end;

the bristle carrier support extends from said head to a point between the toe of the head and the center of said bristle carrier, where there is a separation between the free, toe end of the bristle carrier support and the bottom surface of the bristle carrier; and the front edge of the bristle carrier has a convex curve arcing away from the face, the convex curve arc extending further away from said face than the separation in a direction transverse to the face.

2. The brush section of claim 1, wherein said bristle carrier has one finger extending therefrom.

3. The brush section of claim 2, wherein the face of said bristle carrier is generally egg-shaped.

4. The brush section of claim 1, wherein said carrier has two fingers extending therefrom.

5. The brush section of claim 1, wherein said carrier has three fingers extending therefrom.

6. The brush section of claim 1, wherein the convex curve has a radius of curvature of at least about 1 mm.

7. The brush section of claim 1, wherein the free toe end is configured as a convex curve arcing away from the face surface.

8. The brush section of claim 7, wherein the convex curve of the free toe end has a radius of curvature of at least about 0.5 mm.

9. The brush section of claim 1, wherein the plurality of bristles tufts extending from the first portion of said face are arranged in generally concentric rings and the bristles tufts extending from the one or more fingers are arranged in rows.

10. The brush section of claim 9, wherein the bristle tufts in said rows are longer than the bristle tufts within the concentric rings of bristle tufts.

11. The brush section of claim 1, wherein the brush section is integrally joined to the handle section.

12. A brush section for an electric toothbrush comprising, a first end having a connector adapted to be joined to a handle section; a second end containing a head, which head terminates in a toe and contains a bristle carrier support having an upper surface, the head and connector are generally aligned along the longitudinal axis of the toothbrush; a single, unitary bristle carrier which is centrally supported by rotational means from the upper surface of a said bristle carrier support; which bristle carrier support has a first end integral with the head and a second free, toe end; the bristle carrier support extends from said head to a point between the toe of the head and the center of said bristle carrier; the bristle carrier has a front edge which is convex with respect to said connector, which convex front edge arcs transversely further from the longitudinal axis of said toothbrush than any point on the upper surface of said bristle carrier support, such that in use the users lip or gingival tissue will not be pinched between the front edge of the bristle carrier and the upper surface of the bristle carrier support.

13. The brush section of claim 12, wherein the free toe end is a convex arc in relation to said connector.

\* \* \* \* \*